United States Patent [19]

Nakatani et al.

[11] Patent Number: 5,011,935

[45] Date of Patent: Apr. 30, 1991

[54] IMIDAZOLE ETHER COMPOUNDS

[75] Inventors: Keiichi Nakatani; Nobuyasu Nakasugi, both of Kyoto, Japan

[73] Assignee: San-Apro Limited, Tokyo, Japan

[21] Appl. No.: 371,774

[22] Filed: Jun. 27, 1989

[30] Foreign Application Priority Data

Jun. 27, 1988 [JP] Japan .................. 63-158919

[51] Int. Cl.$^5$ .......................... C07D 403/12
[52] U.S. Cl. ...................... 548/336
[58] Field of Search ........................ 548/336

[56] References Cited

U.S. PATENT DOCUMENTS 3,330,782  7/1967  Poppelsdorf ................ 521/115
3,383,351  5/1968  Stamberger ................ 524/762

FOREIGN PATENT DOCUMENTS 2250345  4/1973  Fed. Rep. of Germany ...... 548/336

OTHER PUBLICATIONS

Chemical Abstracts, 72:66866e (1970)[V. Sunjic et al., *Acta Pharm. Jugoslav*, 1969, 19(2), 65-9].

*Primary Examiner*—John M. Ford
*Attorney, Agent, or Firm*—Michael Leach; James C. Simmons; William F. Marsh

[57] ABSTRACT

A urethane catalyst which is an imidazole ether compound of the formula

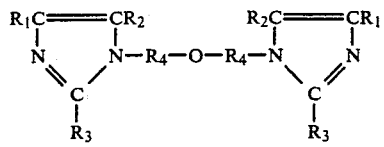

where $R_1$, $R_2$ and $R_3$ are independently hydrogen, methyl or ethyl and $R_4$ is ethylene, n-propylene or isopropylene.

The imidazole compounds provide for delayed initiation while maintaining an acceptable cure time in the production of polyurethane foam.

2 Claims, No Drawings

IMIDAZOLE ETHER COMPOUNDS

TECHNICAL FIELD

The present invention relates to nitrogen-containing compounds as urethane catalysts and, in particular, imidazole compounds as catalysts for the urethane reaction.

BACKGROUND OF THE INVENTION

As catalysts for the production of urethane foam, there have been used tin catalysts and amine catalysts. In view of the restriction on chlorofluorocarbon (CFC) gases, there has been a demand for an amine catalyst which could strongly accelerate the reaction between water and the isocyanate group (foaming catalysts).

Amine catalysts have a strong foaming property in comparison with tin catalysts. Above all, as especially strong foaming catalysts, there are N,N,N',N',N''- pentamethyl diethylenetriamine and bis(2-dimethylaminoethyl) ether.

However, the above two catalysts have high vapor pressure and objectionable odor so that they deteriorate the working environment in the urethane production process. Further, the former has a large temperature dependency, and at the initial stage of foaming, i.e., when the reaction temperature is low, it remarkably accelerates the foaming reaction, but when the reaction temperature rises, it also accelerates the resin-forming reaction so that t becomes difficult to keep the balance between the two reactions. Further, for both catalysts, when either one is solely used in a urethane foaming recipe, the time from the start of stirring of the raw materials to the start of foaming (cream time) becomes extremely short. Therefore, when sufficient amount of catalyst is added to ensure a time for completion of curing (demold time) which is preferred for the urethane foam production process, it becomes impossible to secure the stirring time necessary for the even mixture of the urethane foam materials.

SUMMARY OF THE INVENTION

The present invention provides a urethane catalyst which is an imidazole ether compound of formula (1)

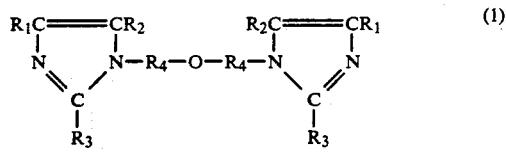  (1)

in which $R_1$, $R_2$, and $R_3$ are each hydrogen, methyl or ethyl and $R_4$ is ethylene, n-propylene or isopropylene.

These imidazole ether compounds can be prepared by reacting the appropriate imidazole compound of formula (2) with either a glycol compound of

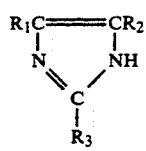  (2)

with either a glycol compound of formula (3)

HOR$_4$—O—R$_4$OH  (3)

or a bis(haloalkyl) ether compound of formula (4)

XR$_4$—O—R$_4$X  (4)

where X is a halogen such as chlorine or bromine.

The imidazole ether compounds of the invention are suitably used to produce a urethane foam by reacting polyisocyanate with polyol in the presence of a foaming agent, a catalyst and other auxiliary agents. The imidazole ether compounds provide for delayed initiation (cream time) while maintaining acceptable cure time (gel and/or tack free time).

DETAILED DESCRIPTION OF THE INVENTION

The present invention provides bis(imidazolyl alkyl)ether of the formula (1):

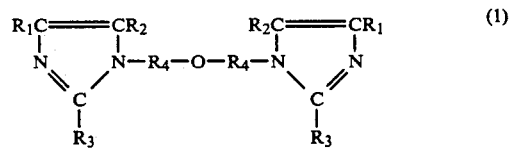  (1)

wherein $R_1$, $R_2$ and $R_3$ are each hydrogen or a $C_1$-$C_2$ alkyl group, and $R_4$ is a $C_2$-$C_3$ alkylene group.

More specifically, the present invention provides 1,1'-(oxydiethylene)bis(2-methyl imidazole) wherein $R_3$ is a methyl group, $R_4$ is an ethylene group, and $R_1$ and $R_2$ are each hydrogen.

Other examples of the compounds of the formula (1) are 1,1'-(oxydiisopropylene)bis(2-methyl imidazole); 1,1'-(oxydiethylene)bis[2-ethyl4(5)-methyl imidazole]; 1,1'-(oxydiisopropylene)bis[2-ethyl-4(5)-methyl imidazole], etc. The acids to be used for forming the salts of the imidazole ether compounds are organic and inorganic acids, which include carboxylic acids (e.g., fatty acids such as formic acid, acetic acid, octyl acids, etc., dicarboxylic acids acids such as adipic acid, etc.), aromatic carboxylic acids (e.g., benzoic acid, phthalic acid, etc.), phenols (e.g., phenol, catechol, etc.), sulfonic acids (e.g., p-toluenesulfonic acid, etc.), carbonic acid, mineral acid, and the like.

The present invention compound, i.e., the imidazole ether compound of formula (1), may be prepared by subjecting the imidazole compound of formula (2) and the glycol compound of formula (3) to a dehydration reaction.

  (2)

HOR$_4$—O—R$_4$OH  (3)

wherein, in formulas (2) and (3), $R_1$, $R_2$ and $R_3$ are each hydrogen, methyl or ethyl group, and $R_4$ is ethylene, n-propylene or isopropylene group.

To effect the dehydration reaction, the above compounds are subjected to heating in the presence of an acid catalyst of Lewis acid such as phosphoric acid, hydrochloric acid, sulfuric acid, p-toluenesulfonic acid, antimony trioxde, phosphorus oxychloride, etc. The molar ratio of the imidazole compound [formula (2)] to the glycol compound [formula (3)] is stoichiometrically 2:1, but, in order to avoid formation of mono(imidazolylalkyl) substituted glycol compound, the molar ratio is preferably 2~4:1. As the azeotropic solvent in the dehydration reaction, hydrocarbon compounds such as benzene, toluene, xylene, etc., may also be used. The amount of the azeotropic solvent to be used is 5~50% (hereinafter by weight), preferably 10~100%, based on the amount of the imidazole compound. The acid catalyst is used by 1~50%, preferably 5~30%, to imidazole compound. The reaction temperature is 60°~300° C., preferably 100°~250° C. The reaction is normally carried out in liquid phase using an ordinary stirring type reaction vessel by heating under ordinary pressure or under elevated pressure. Water produced during the reaction may be removed outside the reaction system together with the azeotropic solvent. The reaction time, though variable by the reaction temperature and the like, is about 2 to 15 hours. After completion of the reaction, the objective compound of formula (1) may be isolated by a conventional method such as distillation.

The present invention compound, i.e., imidazole ether compound of formula (1), may also be produced by a dehydrohalogenation reaction between the imidazole compound of the above formula (2) and the bis(-haloalkyl)ether compound of formula (4)

$XR_4-O-R_4X$ (4)

wherein X is Cl or Br, and $R_4$ is ethylene, n-propylene or isopropylene group.

In the dehydrohalogenation reaction there is usually used, as acceptors of hydrohalogenic acid, amines such as triethylamine, pyridine, imidazole compound, etc., and salts of weak acids such as NaOH, KOH. What is particularly preferred is to use the imidazole compound for the reaction in excess amount and have the excess amount act as the acceptor. The reaction temperature is from room temperature to 150° C., preferably from 50° to 80° C. The reaction time, though variable depending on the reaction temperature or the like, is 2 to 15 hours. After completion of the reaction, the reaction product can be isolated by a conventional procedure, e.g., by distillation.

The imidazole ether compound of the present invention can be used solely as a catalyst for production of flexible, rigid and semi-flexible urethane foams or elastomers. If necessary, it may be used together with other known catalysts. Examples of other catalysts are 1,4-diazabicyclo-(2,2,2)octane; 1,3,5-tris(3-dimethylaminopropyl)hexahydro-s-triazine; N,N,N',N'-tetramethylhexamethylenediamine; N,N,N-tris(dimethylaminopropyl)amine; N-methyl-N,N-bis(dimethylaminopropyl)amine; N-methyldicyclohexylamine; 1,2-dimethylimidazole; 1,8-diazabicyclo(5,4,0)undecene-7, etc.

The ratio of the catalyst mixture of the present invention to the above amine catalyst in co-use is usually 1:10~10:1, preferably 1:4~4:1 by weight.

The above catalyst mixture may be co-used with a metal catalyst such as stannous octoate, dibutyltin dilaurate, mercaptan tin, etc. The ratio of co-use is 1:5~1:0.001, preferably 1:1~1:0.01.

The polyisocyanates and polyols to be used in the present invention include all those which are normally used for the production of the rigid, semi-flexible, and flexible polyurethane foams.

Polyisocyanates include aromatic isocyanates such as toluene diisocyanate, diphenylmethane diisocyanate, etc., aliphatic isocyanates such as hexamethylene diisocyanate, isophorone diisocyanate, etc., and their modification products (e.g., partial carbodiimide or isocyanurate modified product) and free isocyanate-containing prepolymers by the reaction of them with the active hydrogen compounds.

Of these polyisocyanates, the preferred one is aromatic polyisocyanate.

Examples of polyols are high molecular weight polyol such as polyether polyol which has a structure of addition of alkylene oxides (e.g., ethylene oxide, propylene oxide, etc.) to water or polyhydric alcohol, glycol such as ethylene glycol, propylene glycol; polyol having 3 or more OH groups such as glycerin, trimethylol propane, triethanolamine, pentaerythritol, sorbitol, sucrose, etc. or to amine compound (e.g., ethylene diamine, diethylene triamine, toluene diamine, xylene diamine, piperazine, N-aminoalkylpiperazine, N,N-dimethylaminoalkylamine, cyclohexylenediamine, etc.); polymer polyols may be reacting sad polyether polyol with ethylenically unsaturated monomer (acrylonitrile, styrene, methyl methacrylate, butadiene, etc.) (disclosed in U.S. Pat. No. 3,383,351); polyester polyols made by the reaction between the polycarboxylic acid (succinic acid, maleic acid, sebacic acid, adipic acid, fumaric acid, phthalic acid, dimeric acid, etc.) and the above polyhydric alcohols; and a mixture of two or more of them.

Of these polyols, the preferred ones are polyether polyols and polymer polyols.

In the present invention, there may be used if necessary a cross-linking agent such as a low molecular weight polyol [triethanolamine, diethanolamine, ethylene glycol, diethylene glycol, butane diol, trimethylol propane, glycerin, p-bis(2-hydroxyethyl)phenylene ether, etc.] and polyamine (toluenediamine, xylenediamine, diaminodiphenylmethane, methylene-bis-o-chloraniline, etc.).

Examples of the foaming agent to be used in the present invention are water and halogen-substituted aliphatic hydrocarbon foaming agent (Freon gas, methylene chloride, etc.)

There may be used if necessary surfactant (silicone cell conditioner, etc.), colorant, filler, stabilizer, etc.

The amount of the catalyst to be used in the process of the present invention is normally 0.01 to 10 parts by weight, preferably 0.1 to 5 parts by weight, based on 100 parts by weight of polyol. When the amount of the catalyst is 0.01 parts by weight or less, the catalyst activity is low, and too much time is required for the reaction. When the amount is 5 parts by weight, the resulting urethane foam shows lowering in physical property, especially in compression strength (ILD).

The production method of the present invention may be the same as the conventional method, to which either of the one-shot process or the pre-polymer process may be applicable. It is useful for the production of flexible, rigid, and semi-flexible foams.

Hereinafter, the present invention is explained by way of examples, to which it is not to be limited.

EXAMPLE 1

Comparison of activity and behavior of the present invention catalyst

| Foaming Recipe | (Part by weight) |
|---|---|
| SU-464 *1 | 80 |
| ED-450 *2 | 20 |
| Water | 0.5 |
| SH-193 *3 | 1.5 |
| Freon-11 | 37 |
| Amine catalyst | as noted below |
| MDI-CR200 *4 | 110 (INDEX display) |

*1 Sugar polyol made by Mitsui Toatsu Kagaku (K.K.) (OH-V: about 440)
*2 Amine polyol made by Mitsui Toatsu Kagaku (K.K.) (OH-V: about 450)
*3 Silicone cell conditioner made by Toray (K.K.)
*4 Crude MDI made by Mitsui Toatsu (K.K.)

Using the above foaming recipe, foams were generated by an ordinary process in a box having a dimension of 15×12×20 cm (height) at the material temperature of 20° C. with the polyol 50 g scale, and the processing time [cream time (ct), gel time (gt), tack-free time (tft)] was measured. The results are shown in Table 1.

TABLE 1

| | | Processing Time of Catalysts (Sec.) | | |
|---|---|---|---|---|
| Catalyst | (pbw) | ct | gt | tft |
| Present invention #1 | (4.0) | 34 | 85 | 95 |
| Comparative Example #2 | (4.0) | 7 | 82 | 105 |
| Comparative Example #3 | (2.0) | 4 | 88 | 95 |

*1 1,1'-(oxydiethylene)bis(2-methyl imidazole) [catalyst of present invention]
*2 bis(2-dimethylaminoethyl)ether
*3 N,N,N',N',N''-pentamethyl diethylene triamine As apparent from Table 1, using the catalyst of the present invention, the gel time is 85 seconds, being nearly the same as those of the two comparative catalysts, but the cream time is longer by 5 to 8 times than those of the latter. Accordingly, in the present invention catalyst, it is possible to secure the stirring time necessary for even mixing of the materials.

Similar results were obtained in the case where 1,1'-(oxydi-isopropylene)bis(2-methyl imidazole) was used as a catalyst.

EXAMPLE 2

Peparation of 1,1'-(oxydiethylene)-bis(2-methyl imidazole) (dehydration reaction)

2-Methyl imidazole (279 g; 3.4 moles), diethylene glycol (159 g; 1.5 mole), toluene (30 g), and 85% phosphoric acid (20 g; 0.17 mole) were charged in a flask equipped with a stirrer, a thermometer, and a distillation column, and the mixture was stirred at 240°~250° C. for 16 hours. Water produced during that time was distilled out by azeotropic distillation with toluene, and after fractionation the toluene was reflexed. The resulting product was incorporated with an aqueous solution of 48% sodium hydroxide (28.8 g; 0.35 mole) and subjected to distillation under reduced pressure of 1 mm Hg at 210°~215° C. to give a fraction of 239 g (yield, 68% based on diethylene glycol). Total amine value: 465 (theoretical value: 479). $^1$H—NMR (DMSO—$d_6$, δppm)

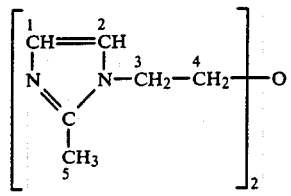

| 1 or 2 | 2H | s | 6.68 (ppm) |
|---|---|---|---|
| 2 or 1 | 2H | s | 6.93 |
| 3 $CH_2$ | 4H | t | 3.58 |
| 4 $CH_2$ | 4H | t | 3.97 |
| 5 $CH_3$ | 6H | s | 2.22 |

EXAMPLE 3

Preparation of 1,1'-(oxydiethylene)-bis(2-methyl imidazole) (dehydrohalogenation reaction)

2-Methyl imidazole (65.6 g; 0.8 mole) and 2-chloroethyl ether (28.6 g; 0.2 mole) were charged in a flask equipped with a stirrer, a thermometer, and a cooling tube, and were reacted at 60°~70° C. for 5 hours. The reaction product was subjected to distillation under reduced pressure of 1 mm Hg at 210°~215° C. to give a fraction of 28.1 g (yield, 60% based on 2-chloroethyl ether). Total amine value: 467.

In the same manner as in Example 2, through 1H-NMR, the product was confirmed to be 1,1'-(oxydiethylene)bis(2-methyl imidazole).

EXAMPLE 4

Preparation of urethane foam

Polyol having a molecular weight of 3000 (propylene oxide addition product of glycerin, SANNIX GP-3000 made by Sanyo Kasei Kogyo, OH-value 56) [100 parts (hereinafter to be "part by weight"), 1,1'-(oxydiethylene)bis(2-methyl imidazole) (0.1 part), water (4.5 parts), silicon L-520 (2 parts), and stannous octoate (0.34 part) were added. To the resulting mixture, TDI-80 (54.8 parts) was added, and the mixture was stirred with a high speed stirrer for 7 seconds, after which the contents were transferred to a carbon box. In a rise time of 82 seconds, a good flexible urethane foam was obtained.

The novel imidazole ether compound of the present invention has a lower vapor pressure than the conventional foaming catalysts such as N,N,N',N',N''pentamethyldiethylene triamine (bp, 201° C./atm.), bis(2-dimethylaminoethyl)ether (bp, 191° C./atm.), etc., namely, it has a high boiling point (210°~215° C./1 mm Hhg), and is almost odorless. Further, notwithstanding the fact that it has almost the same gel time and tack-free time as the above two known foaming catalysts, it shows a long cream time. Accordingly, it shows good workability and is useful as a catalyst for producing urethane foams.

INDUSTRIAL APPLICATION

The present imidazole ether compounds are useful as urethane catalysts in the production urethane foam products.

We claim:

1. An imidazole ether compound of the formula (1):

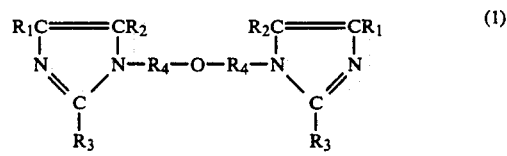

wherein $R_1$, $R_2$ and $R_3$ are each hydrogen, methyl or ethyl group, and $R_4$ is ethylene, n-propylene or isopropylene group.

2. The compound according to claim 1 which is 1,1'-(oxydiethylene)-bis(2-methyl imidazole), wherein, in formula (1), $R_1$ and $R_2$ are each hydrogen, $R_3$ is methyl group and $R_4$ is ethylene group.

* * * * *